(12) United States Patent
Gupton

(10) Patent No.: US 6,468,254 B2
(45) Date of Patent: *Oct. 22, 2002

(54) OSTOMY BAG UNDERGARMENT

(75) Inventor: Kenneth Gupton, 9535 Fairmead Dr., Charlotte, NC (US) 28269

(73) Assignee: Kenneth Gupton, Charlotte, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/324,470

(22) Filed: Jun. 2, 1999

(65) Prior Publication Data

US 2002/0016578 A1 Feb. 7, 2002

(51) Int. Cl.[7] .................................................. A61F 5/44
(52) U.S. Cl. ....................................................... 604/345
(58) Field of Search ................................ 604/322, 327, 604/331, 332–345

(56) References Cited

U.S. PATENT DOCUMENTS

| 4,145,763 A | * | 3/1979 | Abrams et al. ................. 2/403 |
| 4,300,241 A | | 11/1981 | Shaull |
| 4,446,575 A | | 5/1984 | Davis |
| 4,533,355 A | * | 8/1985 | Fair ............................ 604/345 |
| 4,597,110 A | | 7/1986 | Smith, Sr. et al. |
| 4,637,078 A | | 1/1987 | Southwell |
| 4,888,006 A | * | 12/1989 | Beaupied ..................... 604/345 |
| 5,546,608 A | | 8/1996 | Russano |
| 5,607,412 A | * | 3/1997 | Brown ........................ 604/332 |
| 5,843,054 A | * | 12/1998 | Honig ........................... 60/345 |

* cited by examiner

Primary Examiner—Anhtuan T. Nguyen
Assistant Examiner—Ann Y. Lam

(57) ABSTRACT

A shorts-type undergarment with an inner pocket (1) secured to the waistband (6) having a U-shaped cutout(2) where the flange (8*a*) of an ostomy bag (8*c*) is situated. Said inner pocket (1) is attached to the waistband(6) and holds and ostomy bag(8*c*). At the bottom of the inner pocket (1) is a horizontal strip of oppositely mated Velcro strips(9) which can be detached to allow the exit of the bag's tube to dispose of the accumulated bodily fluids. It has two vertical openings on the front of the shorts. The first opening,4, is located at the bottom of the crotch and extends upward. This opening, 5, allows for the insertion of a catheter. The second opening, is an access panel,4, which is opened by pulling back a long vertical strip of Velcro®, 3, attached to a corresponding strip of oppositely mated Velcro®, 2, which horizontally extends partially across one front side. The patient is able to retain a high degree of modesty and dignity, when the catheter is attended to by medical personnel. Since the catheter is secured, in a straight pathway, there is a decreased likelihood the patient will develop secondary medical complications like urinary tract infections, discomfort and irritation associated with a catheter which is not properly secured.

1 Claim, 3 Drawing Sheets

OSTOMY BAG UNDERGARMENT

BACKGROUND—FIELD OF INVENTION

This invention relates to an undergarment which provides an inner compartment to hold an ostomy bag. Additionally, it provides easy access to the crotch area for examination, or treatment, by medical personnel when the patient is catheterized. It affords the patient a sense of dignity and modesty by allowing them to wear an undergarment while fitted with an ostomy bag. The inner compartment has an opening at the bottom which detaches to allow the user to empty the ostomy bag without taking off the undergarment. The design has the additional effect of keeping the catheter securely aligned, in a straight path, to avoid harmful sideways movement. This movement creates irritation and increased risk of urinary tract infections.

BACKGROUND—DESCRIPTION OF PRIOR ART

Heretofore many different arrangements were used to provide access to the crotch region. However, no undergarment has the capacity to house an ostomy bag. There is a specific need for an undergarment which allows the user to simultaneously wear an ostomy bag. This allows the patient to maintain his sense of modesty and dignity. The prior art contains examples of this concept but fails to produce the desired result due to the necessity of removing the entire frontal panel of the undergarment and none have a compartment for an ostomy bag. This results in exposing the entire genital and anal area to the public. Another unique need, not addressed by the prior art, is the necessity of holding the ostomy bag firmly in place to reduce the risk of it becoming detached from the skin. Additionally, by enclosing the bag in fabric, it reduces the chances of skin irritation due to the heat of the expelled body fluids directly touching the skin. The following is a discussion of these arrangements and their drawbacks:

One arrangement involved simply having an open crotch portion with no covering. Shaull U. S. Pat. No. 4,300,241 (1981) is specifically designed for use by female patients undergoing gynecological examinations. Although suitable for this limited purpose, the opening is much too small to allow medical personnel sufficient access to the crotch area to safely insert a catheter and sanitize the area during routine hygiene maintainence. Additionally, the open design does not afford the patient any degree of privacy because the opening can not be closed. Shaull does not have any compartment for an ostomy bag.

Another arrangement, shown in Smith U. S. Pat. No. 4,597,110 (1986) demonstrates a panty-type undergarment with a horizontal opening at the bottom of the crotch. This invention is not intended to be accessed by medical personnel and does not have a opening for the insertion of a catheter. Smith does not have any compartment for an ostomy bag.

Davis U. S. Pat. No. 4,446,575 (1984) utilizes a narrow vertical opening in the rear of the undergarment. Its purpose, like Shaull, is to provide an access panel for a medical examination purposes, specifically, a proctological examination. It would not be functional for access to the frontal crotch region for catheterization. Davis does not have any compartment for an ostomy bag.

Abrams U. S. Pat. No. 4,145,763 (1979) attempts to solve the problem of dual access to the front and back portions of the crotch area. It utilizes two completely separable cloth panels secured by Velcro® tabs. During examination, either tab can be completely removed or rolled up and secured to accommodate access. Unfortunately, the horizontal fastening tabs, at the base of the crotch area, can not be raised very high. This necessitates the unfastening of the side Velcro® tabs which exposes the entire genital area and buttocks of the patient. Abrams does not have any compartment for an ostomy bag.

Russano U. S. Pat. No. 5,546,608 (1996) also employs Velcro® tabs to secure the undergarment. However, like Abrams, it uses many small tabs which are secured to the outside of the garment. Again, like Abrams, the entire undergarment opens up completely but Russano is constructed of one-piece. When the garment is raised, the entire genital area and buttocks of the patient are exposed. This is due to the fact that it is specifically designed for a physically handicapped person whose crotch region is difficult to access. This undergarment employs a flap, located at the bottom of the groin area, which can be raised for the insertion of a catheter. The disadvantage of having a flap in this area is the increased sanitation risk of providing a ready medium on which the discharge of urine and other bodily fluids will collect. Russano does not have any compartment for an ostomy bag.

Like Russano, Southwell U. S. Pat. No. 4,637,078 (1987) is specifically designed for the handicapped. It is also a one-piece undergarment whose front and back crotch portions disconnect. This allows a long one piece undergarment to be opened up completely. Unfortunately, this exposes the entire crotch region exposing the entire genital area and buttocks of the patient. It employs a hook and loop fastening means which connects a triangular shaped panel fitted into a V-shaped notch. Along one side of the notch, a long slit runs at a 45 degree angle into which a catheter may be placed. This is a disadvantageous position for insertion of a catheter. It promotes side-ways movement of the catheter and can cause irritation and further medical urinary problems. Southwell does not have any compartment for an ostomy bag.

OBJECTS AND ADVANTAGES

Accordingly, several objects and advantages of my invention are to hold the ostomy bag firmly in place. This prevents random sideways movement which can irritate the point of attachment to the skin. A major problem the user encounters while wearing the bag is the irritation to the skin from the heat of the expelled bodily fluids. By surrounding the bag with fabric, a barrier is established to substantially decrease the amount of heat the skin receives. Additionally, the undergarment provides a straight secure path into the crotch area, for insertion of a catheter. Easy access to the crotch area, for sanitation and medical purposes, is achieved without changing the straight insertion path of the catheter. The patient is truly given a sense of dignity and modesty by not having his entire crotch and buttocks area exposed while he wears his ostomy bag.

Medically, it is extremely important for the catheter to be stationary and enter the patient from a straight and secure path. If it shifts from side to side, irritation will occur and the catheter may have to be removed. This promotes skin irritation and infections. My invention securely guides the catheter through a straight vertical slit at the bottom of the crotch region to prevent these problems. Another advantage is the retention of this secure opening during sanitation and medical procedures. This is due to the fact of a separate vertical slit, above the opening, which is utilized for these purposes. This allows the catheter to remain stationary while the crotch area is accessed.

This long vertical slit is easily opened by two opposing Velcro® tabs. In one simple motion, as opposed to opening many small tabs, the undergarment is opened from the front. This exposes the catheter. It may then be inserted, removed or the area sanitized. Because the urinary tract is involved, there is a frequent and important need to routinely sanitize the genital area to prevent infections. This necessitates frequent maintenance by medical personnel. The positioning of the opening mechanism, directly above the catheter opening, versus on the side, reduces the likelihood that the catheter will shift sideways and cause irritation. Additionally, it provides instantaneous access for routine observation of the catheter by medical personnel or the patient.

Another advantage is the overwhelming sense of dignity and modesty the patient is afforded by this unique design. Other patents claim this feature but still expose the buttocks, rectum, scrotum and other genital areas when the undergarment is unfastened. My invention positions the bottom of the vertical access panel directly above the vertical slit for the catheter. It continues to run to the very top of the undergarment. This allows the medical personnel to completely expose the front crotch area for catheterization and sanitation. During this process, the buttocks, rectum, scrotum and other genital areas are covered. Additionally, it also allows the patient to easily and modestly check his catheter without taking off his undergarment.

The universal application of my invention is another advantage of the prior art. It is not limited to the handicapped or one sex. It is designed for universal application to any person requiring catheterization. Heretofore, no undergarment has been introduced with could house an ostomy bag.

My invention gives the patient a sense of dignity and modesty by allowing him to wear an undergarment while fitted with an ostomy bag. They do not have to worry about the bag soiling their outergarment, such as a pair of pants or dress. It can be worn for all types of activities. It allows the user to engage in many rigorous activities such as sports, swimming, manual labor which were not possible due to the swaying of the bag. In particular, a unique feature of my invention, due to the opening in the crotch area, allows the user, male or female, to wear it during sexual intercourse. A person fitted with an ostomy bag is genuinely worried about the response of their sexual partner when the bag is naturally inbetween the two of them during sexual intercourse. It is unsightly and contains human excrement which can soil the other person. My invention, allows the user to cover up their ostomy bag thus preventing any unsightly exposure and direct contact to the skin of their partner.

During intercourse, the man's penis can easily exit through the crotch opening. Conversely, for a female user, the crotch opening can be opened wide enough to allow full access to the woman's vaginal area. This allows the user to engage in an important activity which they were restricted from due to important modesty and dignity concerns. Another advantage of my invention that accords modesty and dignity to the user is the fact the user can open up the bottom part of the compartment to allow the bag to be opened to expel the bodily fluids without taking off their pants or shorts. This feature allows the draining of the bag without having to take it out of the undergarment. Thus when in a public restroom, instead of having to lower the user's pants to the floor to access the bag, access can be simply had by opening the bottom of the compartment and the drainage tube exits through the zipper. Or, with a pair of short, nothing is even unzipped and the drainage tube exits the leg of the shorts once the compartment is opened.

BRIEF DESCRIPTION OF THE DRAWING

Drawing one is a view from the outside. (1) denotes where the bottom portion of the inside pocket is located. (2) denotes where the ostomy bag will hang. (3) denotes the elongated Velcro strip (passive end) to which the corresponding aggressive Velcro strip (4) is joined providing access to the inside of the garment. (5) denotes an opening whereby a Foley catheter may exit the undergarment if the patient requires catherterization. (6) denotes an elastic waistband. (7) denotes a hemmed bottom trim.

Drawing 2 is a view from the inside of the undergarment. (1) denotes the entire pocket, (2) denotes the opening in the pocket which the ostomy bag is inserted. (9) denotes the bottom of the inner pocket which opens up by pulling apart corresponding aggressive and passive horizontal strips located on the inside of the bottom of the inner pocket.

Drawing 3 is a view from the inside of the actual pocket and demonstrates how the ostomy bag will be situate inside the pocket. (8) denotes the top of the bag. (8a and 8b) respectively denote the outer and inner edges of the flange which rests securely on the bottom lip of the opening of the pocket (2) (8c) denotes the bottom portion of the bag which hangs at the inside bottom of the pocket.

SUMMARY

My invention is an undergarment which provides a secure inner pocket to house an ostomy bag. Additionally, it provides easy access to the crotch area for patients requiring catheterization. This allows the bag to be held firmly in place thus preventing detrimental sideways movement. This allows the user to engage in many rigorous activities such as sports, swimming and sexual intercourse which the user could not participate in. By encasing the bag in a fabric barrier the heat from the expelled bodily fluids is reduced at the point of contact with the skin. The detachable bottom portion allows the user to conveniently expel the bodily fluids without taking off their outergarments. It affords the user a sense of dignity and modesty while having sexual intercouse. The unique design and placement of the access panel, directly above the slit, reduces the irritation caused by the catheter. Because the panel is secured by just two tabs of passive and aggressive Velcro®, vertically positioned, the catheter may be inspected without promoting side-way movement. During this inspection, and at all other times, the slit firmly holds the catheter in a safe and secure line of entry to the urinary tract. The slit is vertically positioned at the base of the crotch beneath the bottom of the access panel. The positioning of the access panel affords the patient a high level of modesty when the crotch area is exposed.

PREFERRED EMBODIMENT—DESCRIPTION

Operation and use of the undergarment is simple and straightforward. It has an inner compartment which houses an ostomy bag and at its bottom has a detachable horizontal access panel to allow fast convenient drainage of the bodily fluids. It has two vertical openings located on the front of the undergarment to accommodate the insertion of a catheter and provide access to the crotch region. It may be utilized in many settings, including hospitals, nursing homes and home care. The material is cotton but may be made from any other material suitable for this purpose.

Figure 1:
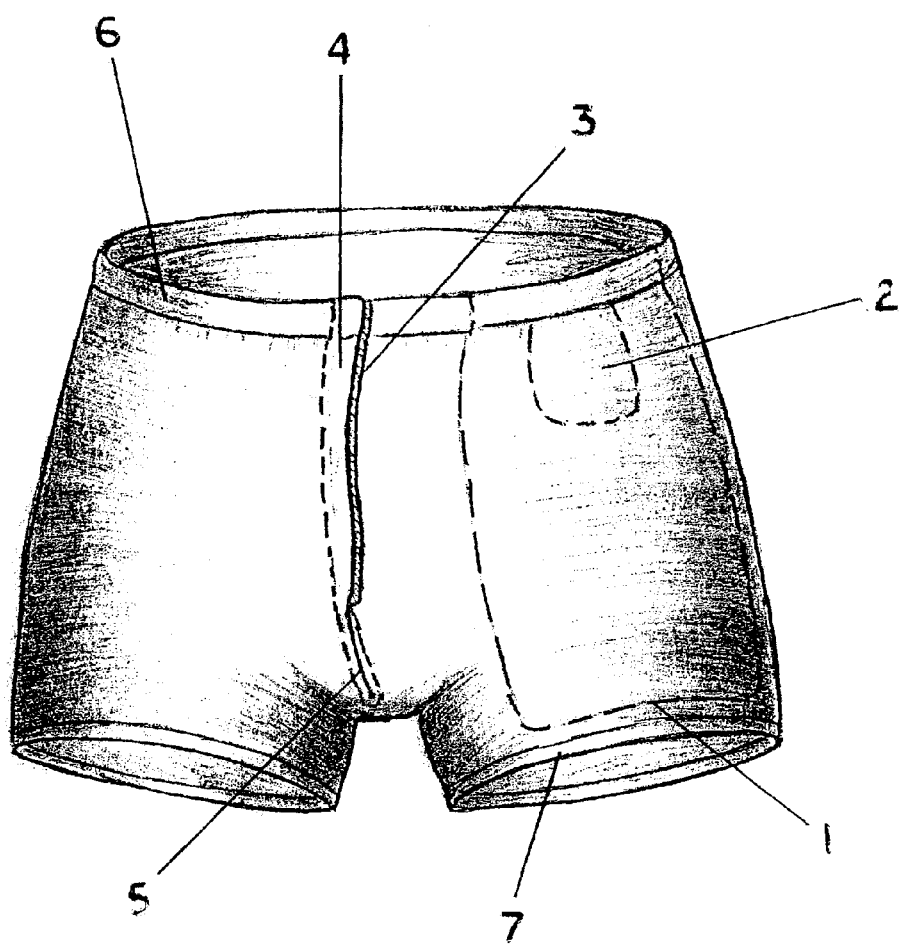
Figure 2:
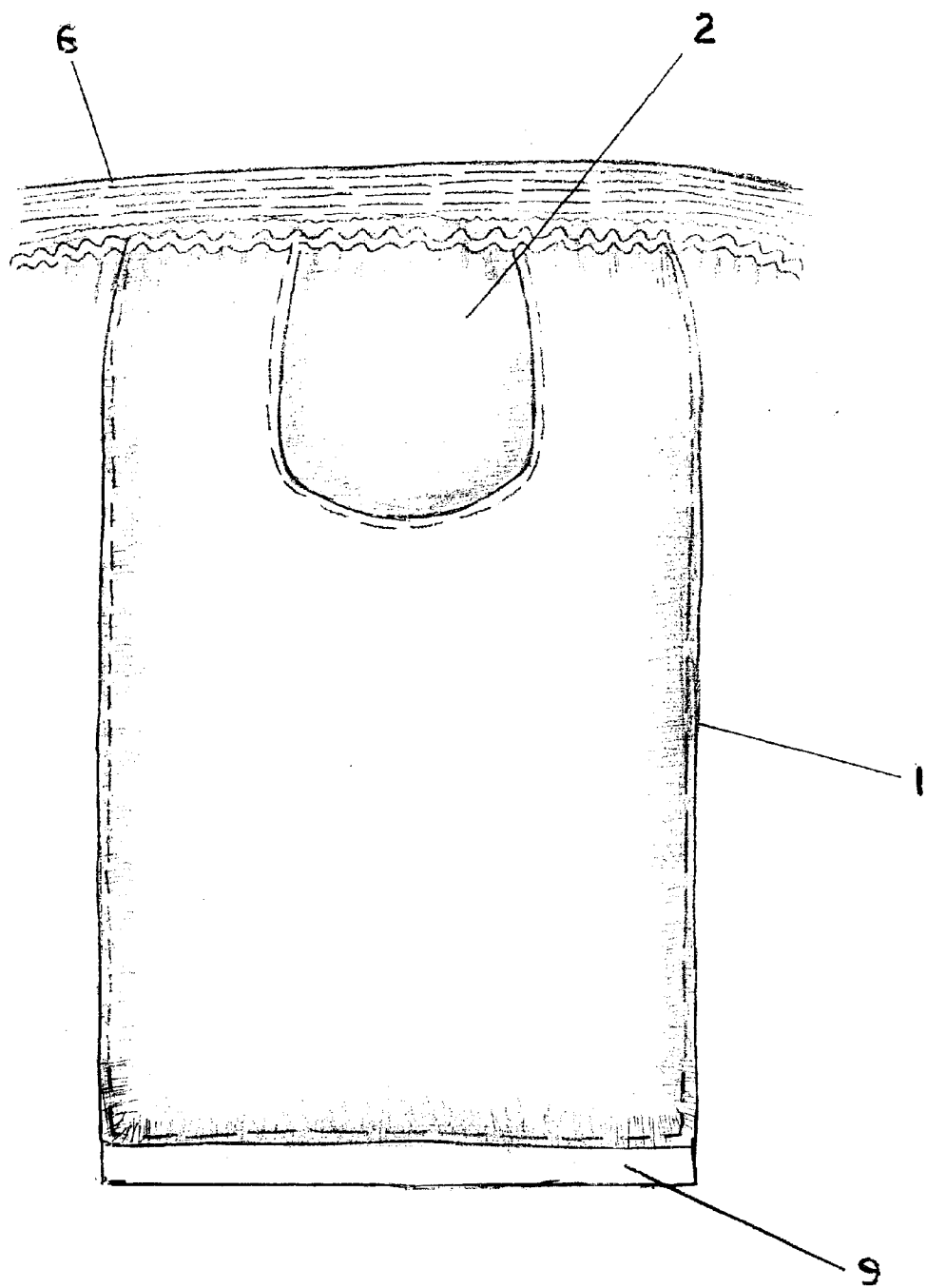
Figure 3:
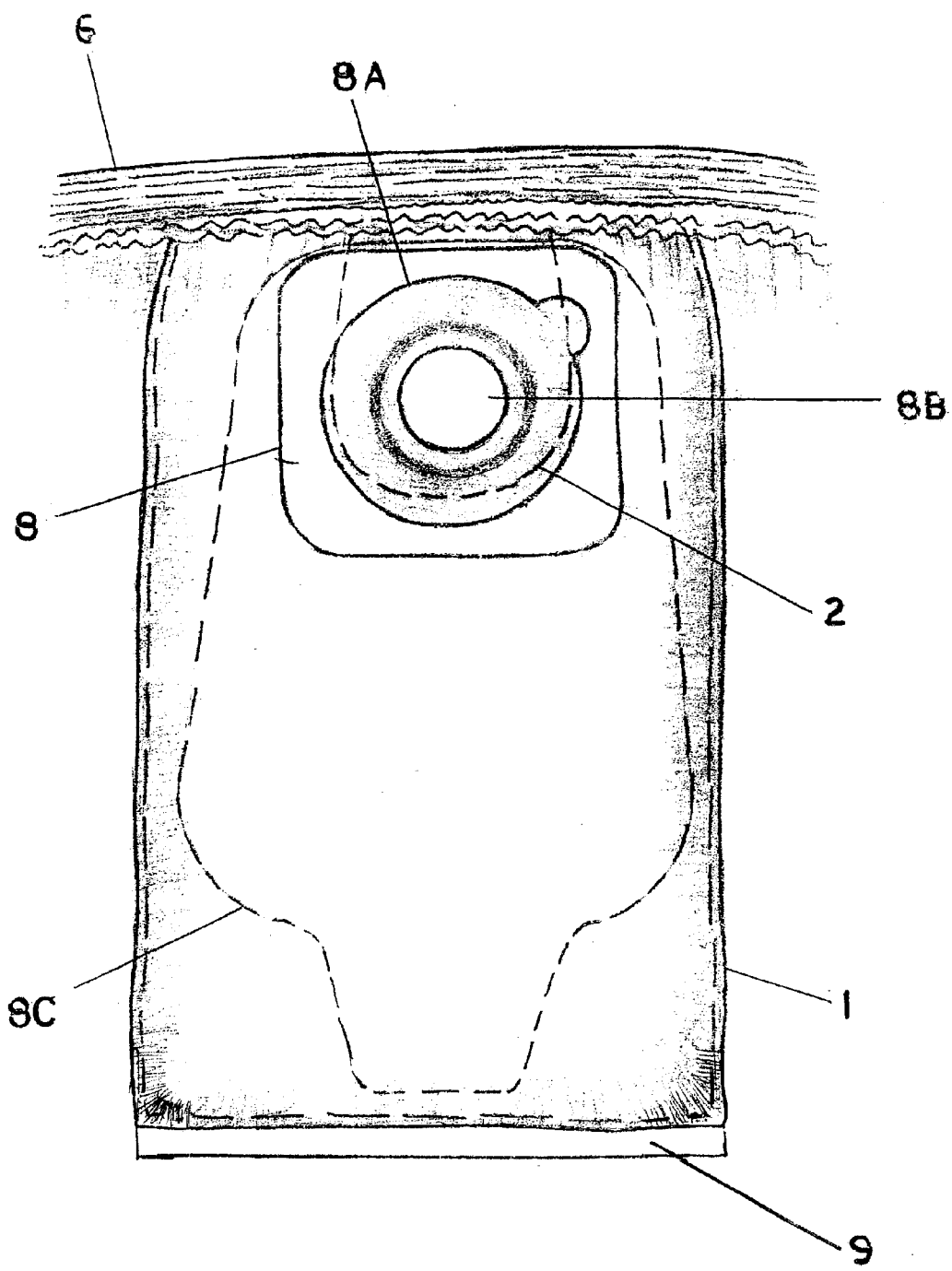

In FIG. 1, the inner pocket (1) hangs to the bottom of the undergarment. It has an opening at the top middle (2) where the flange of the ostomy bag hangs. In the crotch area corresponding strips of passive (3) and aggressive (4) Velcro strips can be pulled apart for access to the crotch region. At the bottom of the crotch area is a vertical slit (5) which allows the insertion of a catheter. (6) denotes an upper elastic waistband and (7) denotes the lower elastic leg band. In FIG. 2, the inner pocket (1) hangs vertically from the horizontal elastic waistband (6). The Flange of the ostomy bag rest comfortably in a U-shaped cutout (2) located in the upper middle of the inner pocket. On the bottom inside of the inner pocket is a horizontal strip (9) of passive and aggressive Velcro which can be unfastened to allow disposal of the accumulated bodily fluids. In FIG. 3, the flange of the ostomy bag (8) is shown along with its outer (8a) and inner (8b) edges located in the U-shaped opening (2). The bottom of the bag (8c) hangs vertically inside the inner pocket (1).

CONCLUSIONS, RAMIFICATIONS AND SCOPE

It can be seen that, according to the invention, the undergarment has an inner pocket sewn to the inside waistband. This pocket has a cutout U-shaped portion, located in the upper middle of the pocket. This allows for an ostomy bag to be inserted into the pocket and its flange securely held in place by the U-shaped portion. At the bottom of the inner pocket is a horizontal strip, on the inside bottom, which has corresponding passive and aggressive strips of Velcro which allows the bottom to be opened so the bag may be drained. This inner pocket holds the bag securely in place and prevents damaging sideways movement of the bag. This allows the user to participate in a wider range of activities such as sports, swimming, manual labor and sexual relations. It accords the user a feeling of security and comfort which gives them a high level of dignity heretofore lacking. By encasing the bag in a fabric, the heat of the bodily excrements is reduced at the point of contact with the skin. This decreases the health problems associate with skin irritation and contact with the fecal matter. The middle access panel employs the use of two Velcro® strips, passive and aggressive, to gain access and closure of the panel. Said panel being located directly above the second vertical slit which allows insertion of a catheter. The unique placement of the two slits, the access panel being directly above the catheter slit, provides many advantages for the patient. These advantages include decreased risk of irritation from side-ways movement, decreased risk of urinary tract infection, easy access to the crotch region and a great sense of modesty for the patient while the catheter is being serviced.

Although the description above contains many specificities, these should not be construed as limiting the scope of the invention but a merely providing illustrations of some of the presently preferred embodiments of this invention. Various other embodiments and ramifications are possible with it's scope.

Thus the scope of the invention should be determined by the appended claims and their legal equivalents, rather than by the examples given.

I claim:

1. An undergarment for hospital, nursing home and homecare use which comprises: an undergarment having a front, a rear, a waist and a crotch; said undergarment having a vertical slit extending from a bottom of the crotch upward to a top of said crotch thereby allowing the insertion of a catheter, and a vertical access opening located and extending directly above said catheter slit to said waist and wherein said opening has two trips of mating corresponding passive and aggressive hook and loop fasteners to open and close said opening when said garment is worn, said undergarment further comprising an inner pocket, attached to the waistband, with a U-shaped cutout which houses the flange of an ostomy bag, the ostomy bag being located inside the inner pocket, the inner pocket having at its bottom a detachable horizontal strip with corresponding passive and aggressive Velcro strips allowing it to be opened to expel accumulated bodily fluids.

* * * * *